United States Patent [19]
Aldrich et al.

[11] Patent Number: 4,727,180

[45] Date of Patent: * Feb. 23, 1988

[54] ANTIHYPERTENSIVE POLYHALOHYDROXYISOPROPYL PHENYLALKANOIC AND PHENYLALKENOIC ACIDS, AMIDES AND ESTERS AND INTERMEDIATES THERETO

[75] Inventors: Paul E. Aldrich, Wilmington, Del.; Gilbert H. Berezin, West Chester, Pa.

[73] Assignee: E. I. Du Pont de Nemours and Company, Wilmington, Del.

[*] Notice: The portion of the term of this patent subsequent to May 22, 2001 has been disclaimed.

[21] Appl. No.: 688,949

[22] Filed: Jan. 4, 1985

Related U.S. Application Data

[63] Continuation of Ser. No. 306,411, Sep. 28, 1981, which is a continuation-in-part of Ser. No. 61,045, Jul. 26, 1979, abandoned.

[51] Int. Cl.[4] ............................................. C07C 69/76

[52] U.S. Cl. ............................ 560/55; 260/410.5; 260/544 D; 260/544 S; 260/544 N; 560/20; 560/23; 560/65; 560/85; 560/106; 558/416; 514/513; 514/532; 514/534; 514/538; 514/553; 514/617; 514/618; 514/619; 562/478; 562/434; 562/438

[58] Field of Search ............... 560/55, 20, 23, 65, 560/25, 106; 260/410.5, 544.12, 544 S, 544 N; 558/416; 574/573, 532, 534, 538, 553, 617, 618, 619; 562/478, 464; 582/438

[56] References Cited

U.S. PATENT DOCUMENTS 4,450,172  5/1981  Yoa ........................................ 560/45

Primary Examiner—Paul J. Killos

[57] ABSTRACT

Polyhalohydroxyisopropyl phenylalkanoic and phenylalkenoic acids, amides, and esters, such as methyl 2-methoxy-4-[2,2,2-trifluoro-1-hydroxy-1-(trifluoromethyl)ethyl]benzenepropanoate, are useful as antihypertensive agents.

26 Claims, No Drawings

ANTIHYPERTENSIVE POLYHALOHYDROXYLISOPROPYL PHENYLALKANOIC AND PHENYLALKENOIC ACIDS, AMIDES AND ESTERS AND INTERMEDIATES THERETO

RELATED APPLICATIONS

This application is a continuation of application Ser. No. 306,411, filed Sept. 28, 1981, which is a continuation-in-part of application Ser. No. 061,045, filed on July 26, 1979, now abandoned.

BACKGROUND OF THE INVENTION

This invention relates to acids and derivatives thereof having useful pharmaceutical properties. In particular, this invention relates to phenylalkanoic and phenylalkenoic acids and derivatives thereof which are useful as antihypertensive agents.

U.S. Pat. Nos. 4,058,612 issued to Neustadt on Nov. 15, 1977 discloses 6-(polyhaloisopropyl)quinazoline-2,4-diones which are useful agents in treatment of mammalian hypertension. The compounds are prepared by reacting 2-(lower alkoxycarbonyl)aniline with a polyhalo acetone or hydrate thereof, followed by reaction of the resulting product with the appropriate isocyanate to form a urea, and hydrolysis of the urea.

U.S. Pat. No. 4,103,018 issued to Neudstadt et al. on July 25, 1978 discloses 2-[4-(polyhalo-2-hydroxy-2-propyl)anilino]-2-oxazolin-4-one and thiazolin-4-ones corresponding thereto, which have useful antihypertensive properties. The compounds are prepared by reaction of the appropriate 4-(polyhalo-2-hydroxy-2-propyl)aniline with a β-chloroethanoyl isocyanate or isothiocyanate and then cyclization of the resultant intermediate.

Many current antihypertensive agents produce unwanted side effects because of undesirable mechanisms of action. For example, mecamylamine is a ganglion blocker; phenoxybenzamide is an α-adrenergic receptor blocker; and reserpine is a catecholamine depletor. Each of these mechanism of action is undesirable because serious side-effects are produced. There is a constant need for antihypertensive agents which do not produce these side effects, which have fewer side effects, or which minimize such adverse side effects.

SUMMARY OF THE INVENTION

According to the present invention there are provided compounds of Formulae I and II, and, when $R_4$ is other than Cl, pharmaceutical compositions containing them and methods of using them to treat hypertension in mammals.

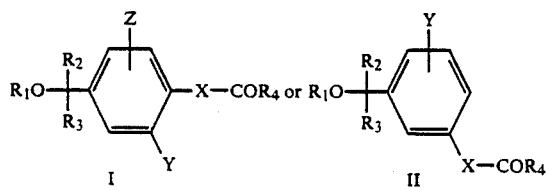

wherein
$R_1$ is H, $C_1$-$C_6$ alkyl, $C_2$-$C_{12}$ acyl, —$CH_2A$— or —C(O)—A;

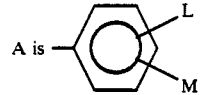

where
L and M are independently H, F, Cl, Br, $NO_2$, $C_1$-$C_4$ alkyl, $C_1$-$C_4$ alkoxy, $CF_2$, $OCF_3$, CN, phenyl or COOR', where R' is H, $CH_3$ or $C_2H_5$;
$R_2$ and $R_3$ are independently $CF_3$, $CF_2Cl$ or $CF_2H$;
$R_4$ is $NR_6R_7$, O—$R_5$, S—$R_5$ or Cl;
$R_5$ is H, $C_1$-$C_{10}$ alkyl, $C_3$-$C_{10}$ alkenyl, A or —$R_8$—A;
$R_6$ and $R_7$ are independently H, $C_1$-$C_6$ alkyl, A or —$R_8$—A;
$R_8$ is $C_1$-$C_6$ alkyl;
Y and Z are independently H, $NO_2$, $C_1$-$C_3$ alkoxy, $C_1$-$C_3$ alkylthio, Cl, Br, F, $C_1$-$C_4$ alkyl, $NH_2$ or $N(CH_3)_2$;
X is

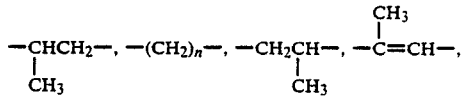

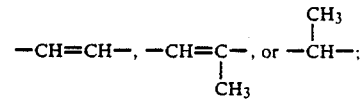

n is 1, 2 or 3;
provided that:
(a) when Y and Z are H, are then X is other than

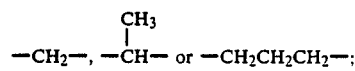

(b) when Y is other than $OCH_3$, then $R_6$ and $R_7$ are $CH_3$; and
(c) when Y and Z are H and X is

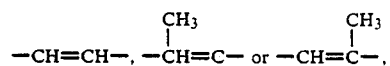

then $R_4$ is other than $NR_6R_7$.

DETAILED DESCRIPTION OF THE INVENTION

Test results indicate that the compounds of the invention, excluding those wherein $R_4$ is Cl, are useful as antihypertensive agents. Compounds wherein $R_4$ is Cl are useful as intermediates to the antihypertensive agents of the invention. The compounds of this invention are believed to lower blood pressure by a desirable mechanism of action, i.e., direct peripheral vasodilation and, therefore have a distinct advantage over antihypertensive agents having undesirable mechanisms of action. Moreover, the compounds of the invention that have been tested have been shown not to produce central nervous system effects such as those encountered in the use of clonidine and α-methyldopa.

Preferred Compounds

Compounds of Formulae I and II are preferred for their antihypertensive activity are those wherein, independently, $R_1$ is hydrogen;
$Y$ is $OCH_3$ or $OC_2H_5$;
$Z$ is H;
$X$ is —$CH_2CH_2$—;
$R_4$ is OH, $OCH_3$, $OC_2H_5$, or $N(CH_3)_2$; or
$R_2$ and $R_3$ are each $CF_3$.

More preferred are compounds of Formula I in which:
$R_1$ is hydrogen;
$Y$ is $OCH_3$ or $OC_2H_5$;
$Z$ is H;
$X$ is —$CH_2CH_2$—;
$R_4$ is OH, $OCH_3$, $OC_2H_5$, or $N(CH_3)_2$; and
$R_2$ and $R_3$ are each $CF_3$.

Specifically or most preferred are the following compounds where Y is $OCH_3$ and Z is H:

(a) 3-{2-methoxy-4-[2,2,2-trifluoro-1-hydroxy-1-(trifluoromethyl)ethyl]phenyl}propanoic acid;

(b) methyl 2-methoxy-4-[2,2,2-trifluoro-1-hydroxy-1-(trifluoromethyl)ethyl]benzenepropanoate;

(c) ethyl 2-methoxy-4-[2,2,2-trifluoro-1-hydroxy-1-(trifluoromethyl)ethyl]benzenepropanoate; and (d) 3-{2-methoxy-4-[2,2,2-trifluoro-1-hydroxy-1-(trifluoromethyl)ethyl]phenyl}-N,N-dimethylpropanamide.

Synthesis

Compounds of Formulae I and II wherein Y is H, Z is H, and X is other than —CH=CH—,

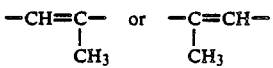

are prepared by a process which comprises first contacting a compound of the formula:

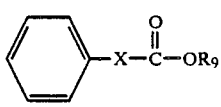

wherein $R_9$ is an alkyl group of 1-4 carbon atoms with a polyhaloketone of the formula

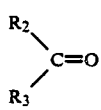

where $R_2$ and $R_3$ are as previously defined in the presence of a suitable catalyst under a pressure near autogenous pressure or above and at a temperature of from about 10° to 150° C., preferably from about 25° to 50° C., for from about 4-16 hours. Suitable catalysts include Friedel-Crafts catalysts, such as $AlCl_3$ or $BF_3$. This reaction is illustrated in Equation 1:

Equation 1

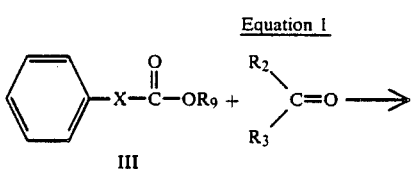

-continued
Equation 1

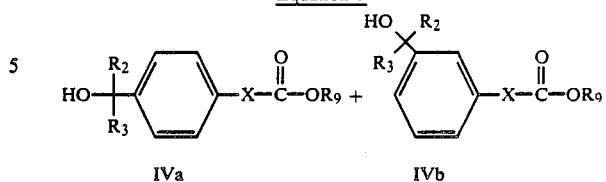

Hydrolysis of the compounds of Formula IVa or IVb with a suitable base, such as sodium hydroxide, in water or other suitable solvent or hydrolysis in equal parts of glacial acetic acid, water, and sulfuric acid gives the corresponding phenylalkanoic acid. When X is just one carbon in length, both IVa and IVb are formed in major amounts; when X is greater in length than one carbon, mainly IVa is produced.

Compounds of Formulae I and II wherein X is —C($CH_3$)=CH— are prepared pursuant to Equation 2. (The meta isomer is analogous.)

Equation 2

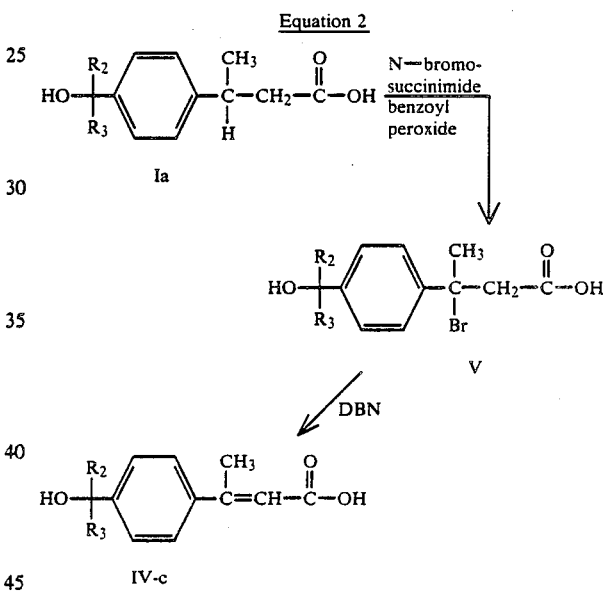

A phenylalkanoic acid prepared by hydrolysis of the product of Equation 1 is contacted with a suitable brominating agent, such as N-bromosuccinimide, in a suitable solvent, such as carbon tetrachloride, in the presence of a suitable catalyst, such as benzoyl peroxide, to obtain a compound of Formula V which is then reacted with a suitable dehydrohalogenation agent, such as 1,5-diazabicyclo[3.4.0]nonene-5(DBN), to give the desired compound of the invention.

Compounds of Formulae I and II wherein Y is $NO_2$ are prepared by contacting an acid of Formulae IVd or IVe with a nitrating agent such as fuming nitric acid in the presence of concentrated sulfuric acid, preferably at 10°-15° C., pursuant to Equation 3.

Equation 3

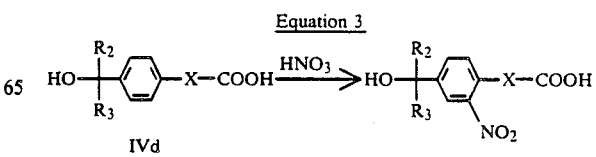

-continued
Equation 3

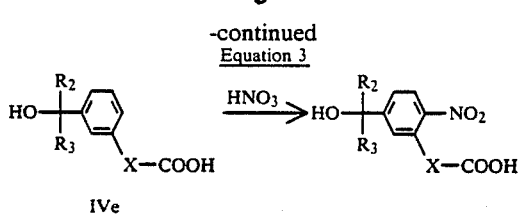

Compounds of Formula I wherein Y is an alkylthio group are prepared as illustrated in Equation 4.

Equation 4

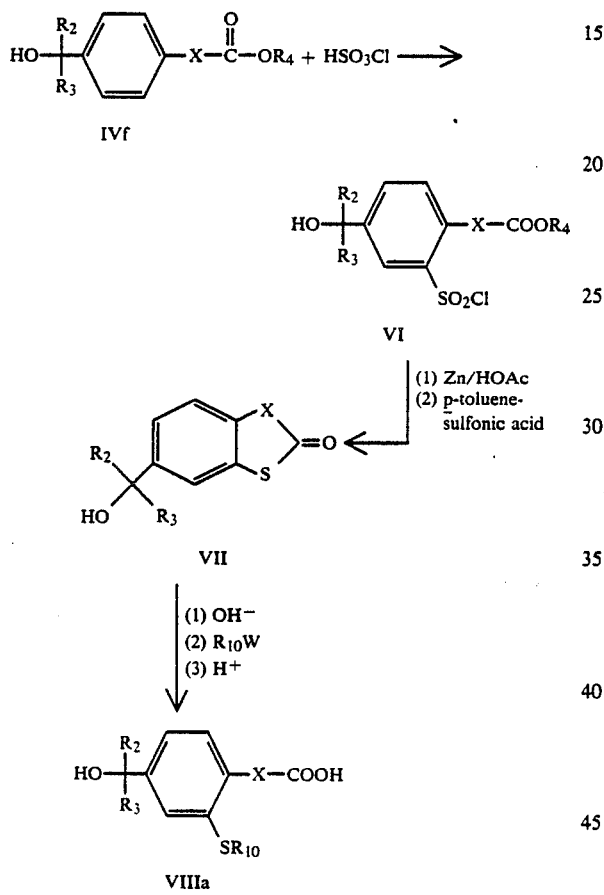

where $R_{10}$ is $C_1$–$C_3$ alkyl. A compound of Formula IVf is contacted with excess chlorosulfonic acid to obtain a sulfonyl chloride derivative, VI. Compound VI is reduced with zinc in acetic acid (HOAc) to obtain a reaction product which is then treated with p-toluenesulfonic acid in toluene to obtain a compound of Formula VII. The compound of Formula VII is contacted with a suitable base, such as sodium hydroxide, in a suitable solvent, such as dimethylacetamide and ethanol, to obtain a reaction product which is then treated with an alkyl halide, $R_{10}W$, where W is chloride, bromide or iodide, to obtain a reaction product that, after acidification, gives a compound of the invention, VIIIa. Compounds IVb analogously result in compounds VIIIb.

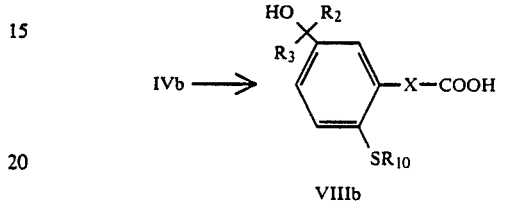

Compounds of Formula I wherein Y and Z are H, and X is —CH=CH— or

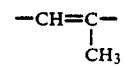

are prepared by another process of the invention. Toluene is contacted with a polyhaloketone of the formula $$\begin{array}{c}R_2\\ \phantom{R}\diagdown\\ \phantom{RRR}C=O,\\ \phantom{R}\diagup\\ R_3\end{array}$$

wherein $R_2$ and $R_3$ are as previously defined, in the presence of a suitable Friedel-Crafts catalyst, such as $AlCl_3$, under a pressure at least equivalent to autogenous pressure of the polyhaloketone at a temperature of from about 10° to 150° C., preferably from 25° to 50° C., to obtain a compound of Formula IXa. The reaction is conveniently performed by utilizing a sealed reactor. The compound of Formula IXa is oxidized with $CrO_3$ in acetic anhydride to obtain a compound of Formula Xa, which is then contacted with malonic acid or methylmalonic acid, preferably in a pyridine-piperidine solution, to obtain a compound of the invention, IVd. The process can be represented as follows:

Equation 5

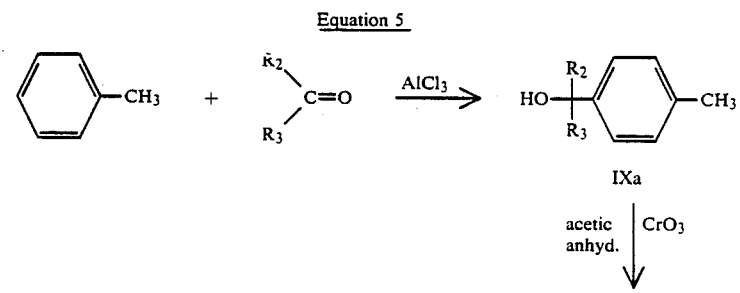

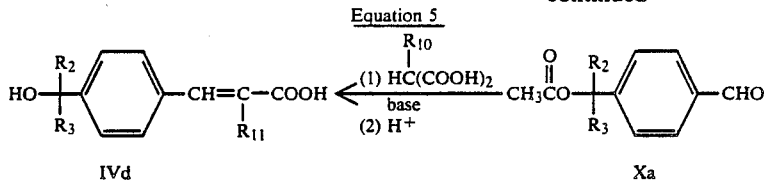

wherein $R_{11} = H$ or $CH_3$.

Compounds of Formula I wherein $R_1$ is H, Z is H and Y is alkoxy of 1-3 carbon atoms are prepared by the process represented by Equation 6. Compounds of Formula II are prepared starting with the para isomer of XI.

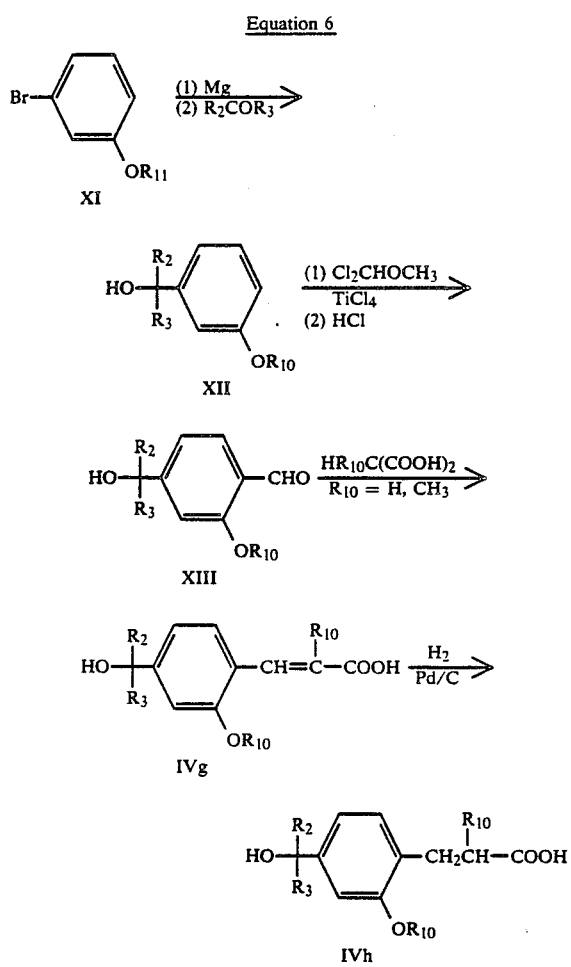

wherein $R_{10}$ is as previously defined.

A meta-bromoalkoxybenzene or meta-chloroalkoxybenzene of Formula XI is treated with magnesium in a solvent such as tetrahydrofuran at a temperature up to the boiling point of the solvent to produce a magnesium halide derivative to which is then added a polyhaloketone to give a compound of Formula XII. The compound of Formula XII is contacted with dichloromethyl methyl ether in a suitable solvent, such as dichloromethane, in the presence of a suitable catalyst, such as titanium tetrachloride, followed by treatment with aqueous HCl to obtain a reaction product represented by Formula XIII. This reaction product is treated with malonic acid or methylmalonic acid in a solvent such as pyridine containing a base such as piperidine to obtain an acid of Formula IVg which can be reduced with hydrogen in the presence of a suitable catalyst, such as 10% palladium on carbon, to produce an acid of Formula IVh.

Compounds of the invention where X is —C(CH$_3$)=CH—, Y is alkoxy of 1-3 carbon atoms, and $R_4$ is $CH_3$ are prepared by a process represented by Equation 7 wherein $R_{10}$ is as previously defined.

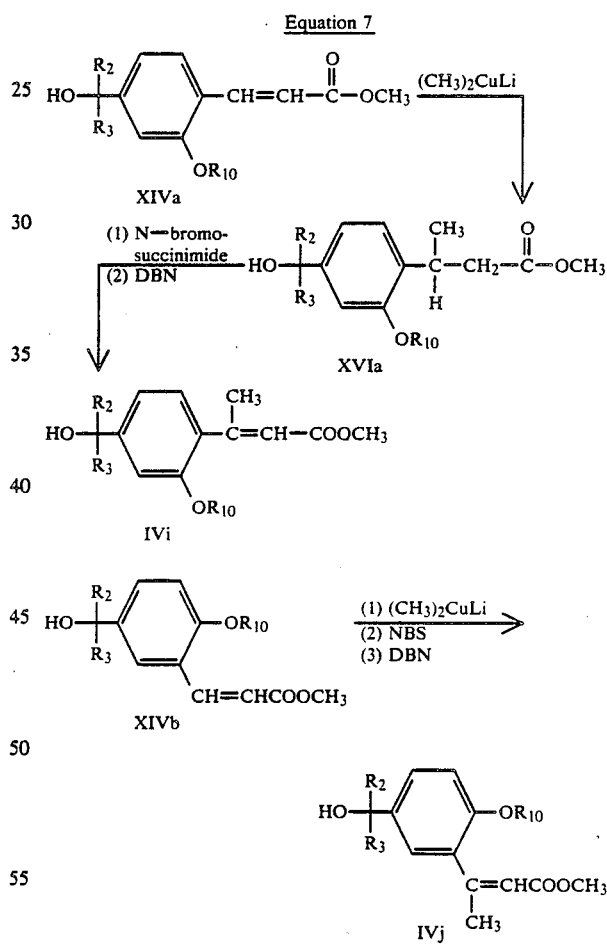

A compound of Formula IVg (from Equation 6) is contacted with methanol to obtain the methyl ester thereof (XIVa) which is then treated with dimethylcopperlithium by using the method of H. O. House and M. J. Umen, *J. Org. Chem.*, 38, 3893 (1973) to give a compound of Formula XVIa. The compound of Formula XVIa is contacted with N-bromosuccinimide in a suitable solvent, such as carbon tetrachloride, in the presence of a suitable catalyst, such as benzoyl peroxide to obtain a reaction product which is then dehydrohalogenated with DBN to give the desired compound of the invention, IVi. The same process converts XIVb to IVj.

2-Alkoxy-4-polyhalohydroxyisopropyl phenylacetic acids of this invention (X=CH$_2$, Y=alkoxy, R$_4$=OH) are prepared by a process illustrated by Equation 8.

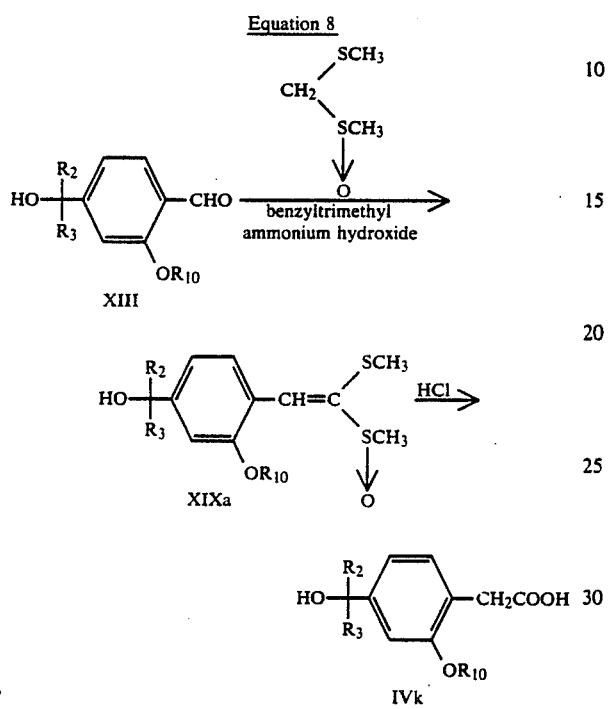

A compound of Formula XIII is contacted with methyl methylthiomethyl sulfoxide in a suitable solvent, such as tetrahydrofuran and in the presence of a suitable catalyst, such as benzyltrimethylammonium hydroxide, to give a compound of Formula XIXa which is then treated with HCl in a suitable solvent, such as dimethoxyethane, to hydrolyze the compound and to obtain a compound of the invention, IVk. Compounds of Formula IVm are prepared analogously:

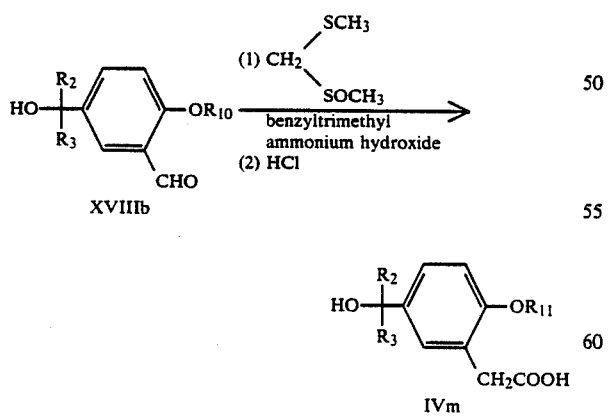

Another approach to preparing the propanoic acids of this invention is by homologation from the corresponding benzeneacetic acids as in Equations 9 and 10.

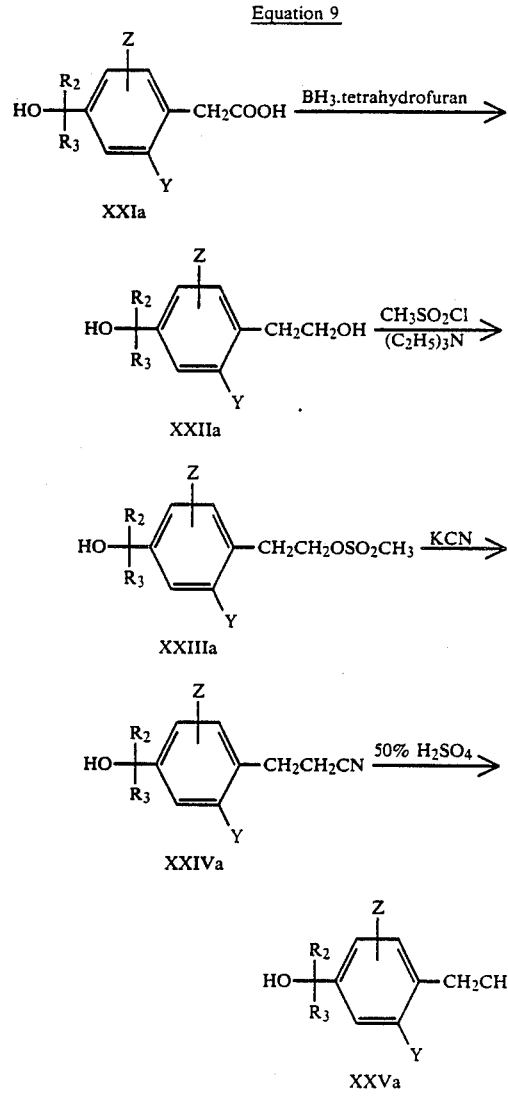

When compounds of Formula I prepared by any of the processes of the invention are acids, they can be converted into esters, thiolesters and N,N-dimethyl amides of the invention in the usual manner via the acid chloride (compounds of Formulae I and II wherein R4=Cl). When the compound prepared by any of the processes of the invention is an ester, it can be converted into the corresponding acid by hydrolysis in the usual manner. Esters wherein $R_1$ is an acyl group are prepared from esters of Formulae I and II where $R_1$ is H by reaction with acid chlorides or anhydrides with or without solvents. Because of the tertiary nature and high acidity of the alcohol group, esterification is rather slow at room temperature but can be greatly accelerated by using high boiling solvents (with or without the addition of a base) or using refluxing pyridine as a solvent and base.

The preparation of compounds of this invention is further illustrated by the following examples in which all temperatures are given in degrees C. and all percentages are by weight unless otherwise stated. As used herein "consisting essentially of" has its customary meaning, i.e., it does not exclude unspecified conditions or materials which do not prevent the advantages of the invention from being realized.

EXAMPLE 1

4-[2,2,2-Trifluoro-1-hydroxy-1-(trifluoromethyl)ethyl]-benzenepropanoic Acid

To 250 ml of dichloromethane are added 267 g (1.5 mole) of ethyl benzenepropionate to obtain a solution which is added to a 1 liter stainless steel reactor equipped with gas inlets having shut off valves. To this solution are added 240 g (1.8 mole) of aluminum chloride. The reactor is sealed, cooled to $-40°$, and evacuated. Then to the reactor is added 249 g (1.5 mole) of hexafluoroacetone, and the bomb is again sealed. The reactor is shaken, allowed to warm up to 25°-30°, and then shaken at this temperature for 8-12 hours. The reactor is vented and the resulting reaction mixture is decanted. The reaction mixture is added to 1 liter of ice and 250 ml of concentrated hydrochloric acid to obtain an aqueous mixture which is then extracted thoroughly with dichloromethane. The resulting dichloromethane solution is washed with water, dried with anhydrous magnesium sulfate, filtered and evaporated at reduced pressure to obtain a residual oil.

This residual oil is heated with 1N NaOH on a steam bath for 3 hours and is then cooled and acidified. Extraction with ether and then evaporation give a residual solid which is then recrystallized from chlorobutane to give 160 g of 4-[2,2,2-trifluoro-1-hydroxy-1-(trifluoromethyl)ethyl]benzenepropanoic acid having a melting point of 79°-81°.

EXAMPLES 2-6

The procedure of Example 1 can be used with the appropriate alkylaryl ester and polyhaloketone to give the compounds listed in Table 1.

TABLE I

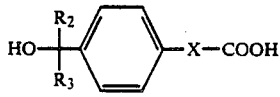

| Ex. | $R_2$ | $R_3$ | X |
|---|---|---|---|
| 2 | $HCF_2$ | $HCF_2$ | $-CH_2CH_2-$ |
| 3 | $CF_3$ | $CF_3$ | $-CH(CH_3)-CH_2-$ (oil) |
| 4 | $CF_3$ | $CF_3$ | $-CH_2-CH(CH_3)-$ (oil) |
| 5 | $HCF_2$ | $HCF_2$ | $-CH(CH_3)-CH_2-$ |
| 6 | $HCF_2$ | $CF_3$ | $-CH_2CH_2-$ |

EXAMPLE 7

3-{4-[2,2,2-Trifluoro-1-hydroxy-1-(trifluoromethyl)ethyl]phenyl}-2-propenoic Acid A: 4-[1-(Acetyloxy)-2,2,2-trifluoro-1-trifluoromethyl)ethyl]benzaldehyde To a solution of 156 g (0.60 mole) of 4-[2,2,2-trifluoro-1-hydroxy-1-(trifluoromethyl)ethyl]toluene in 675 ml of acetic anhydride is added 135 ml of concentrated sulfuric acid at 0°. To the solution stirred at 0° is added a soluton of 168 g (1.68 mole) of chromium trioxide in 750 ml of acetic anhydride dropwise over a two-hour period. After stirring is continued for an additional two hours, the resulting reaction mixture is poured into five liters of ice and is diluted with five liters of water to obtain an aqueous mixture which is allowed to stand for 18 hours. An oily solid with water above it is obtained. Water is decanted from the oily solid. The solid is dissolved in ether to obtain a solution which is washed with water and sodium bicarbonate solution, dried with anhydrous magnesium sulfate, filtered and evaporated at reduced pressure to give an oily solid. The solid is triturated with ether, filtered and recrystallized from chlorobutane to give 60 g of α,α-bis-acetyloxy-4-[1-(acetyloxy)-2,2,2-trifluoro-1-(trifluoromethyl)ethyl]toluene, m.p. 93°-94.6°.

To 130 ml of ethanol are added 60 g (0.15 mole) of α,α-bis-acetyloxy-4-[1-(acetyloxy)-2,2,2-trifluoro-1-(trifluoromethyl)ethyl]toluene and 13.5 ml of concentrated sulfuric acid in 135 ml of water. The resulting solution is stirred and heated at reflux for thirty minutes. The solution is then cooled and extracted with 1 liter of ether to obtain an ether solution which is washed with water and a saturated sodium bicarbonate solution until the washes were basic. The ether solution is dried with anhydrous magnesium sulfate, filtered and evaporated at reduced pressure to give 42 g of 4-[1-(acetyloxy)-2,2,2-trifluoro-1-(trifluoromethyl)ethyl]benzaldehyde. This compound was not further purified but was used directly in the next step.

B: 3-{4-[1-Acetyloxy]-2,2,2-trifluoro-1-(trifluoromethyl)ethyl]phenyl}-2-propenoic Acid To 29 ml of 95% ethanol are added 35 g (0.11 mole) of the compound whose preparation is described in part A, 12.5 g (0.11 mole) of malonic acid, and 2.8 ml of pyridine. The resulting solution is stirred, heated at reflux for 18 hours, and then is evaporated at reduced pressure to obtain a residual oil, which is taken up in ether. The resulting ether solution is washed with 1N hydrochloric acid, dried with anhydrous magnesium sulfate, filtered and evaporated at reduced pressure to give a solid, which is recrystallized from a benzene-hexane mixed solvent to give 30 g of 3-{4-[1-(acetyloxy)-2,2,2-trifluoro-1-(trifluoromethyl)ethyl]phenyl}-2-propenoic acid having a melting point of 144°-147°.

C: 3-{4-[2,2,2-Trifluoro-1-hydroxy-1-(trifluoromethyl)ethyl]phenyl}-2-propenoic Acid To 100 ml of water are added 8 g (0.02 mole) of the compound whose preparation is given in part B and 2 g (0.05 mole) of sodium hydroxide to obtain a reaction mixture which is stirred and heated at reflux for 18 hours. The solution is then cooled and made acid with concentrated hydrochloric acid to obtain a precipitate which is extracted with ether. The resulting ether solution is dried with anhydrous magnesium sulfate, filtered, and evaporated at reduced pressure to give a residual solid which is recrystallized from chlorobutane to give 5.5 g of 3-{4-[2,2,2-trifluoro-1-hydroxy-1-(trifluoromethyl)ethyl]phenyl}-2-propenoic acid having a melting point of 186°–188°.

EXAMPLES 8–11

The procedure of Example 7 can be used with the appropriate substituted benzaldehyde and malonic acid to give compounds listed in Table 2.

TABLE 2

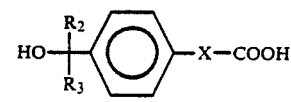

| Ex. | $R_2$ | $R_3$ | X |
|---|---|---|---|
| 8 | $CF_3$ | $CF_3$ | $-CH=C(CH_3)-$ m.p. 125–127° |
| 9 | $CClF_2$ | $CClF_2$ | $-CH=CH-$ |
| 10 | $CF_2H$ | $CF_2H$ | $-CH=C(CH_3)-$ |
| 11 | $CF_2H$ | $CF_2H$ | $-CH=C(CH_3)-$ |
| 12* | $CF_3$ | $CF_3$ | $-CH=CH-$ |
| 13** | $CF_3$ | $CF_3$ | $-CH=CH-$ m.p. 179–182° |

*The starting material 2-fluoro-4-[2,2,2-trifluoro-1-hydroxy-1-(trifluoromethyl)ethyl]toluene can be prepared from 4-bromo-2-fluorotoluene by the Grignard method described in Ex. 43.
**The starting material 3-methoxy-4-[2,2,2-trifluoro-1-hydroxy-1-(trifluoromethyl)ethyl]toluene can be prepared from 4-chloro-3-methoxytoluene by the Grignard method described in Ex. 43 except that the Grignard formation must be carried out at reflux.

EXAMPLE 14

3-Methyl-3-{4-[2,2,2-trifluoro-1-hydroxy-1-(trifluoromethyl)ethyl]phenyl}-2-propenoic Acid This compound can be prepared by the following preparation:

A: Methyl 3-Bromo-3-methyl-{4-[2,2,2-trifluoro-1-hydroxy-1-(trifluoromethyl)ethyl]phenyl}propanoate To a solution of methyl 3-methyl-3-{4-[2,2,2-trifluoro-1-hydroxy-1-(trifluoromethyl)ethyl]phenyl}propanoate, which can be prepared in a manner similar to that described in Example 76, in carbon tetrachloride can be added N-bromosuccinimide and a small quantity of benzoyl peroxide. The resulting mixture can be stirred and heated at reflux until thin layer chromatographic analysis of a reaction sample indicates the reaction to be complete. The succinimide can be removed by filtration and the solvent removed at reduced pressure to give methyl 3-bromo-3-methyl-{4-[2,2,2-trifluoro-1-hydroxy-1-(trifluoromethyl)ethyl]phenyl}propanoate.

B: 3-Methyl-3-{4-[2,2,2-trifluoro-1-hydroxy-1-(trifluoromethyl)ethyl]phenyl}-2-propenoic Acid To a solution of methyl 3-bromo-3-methyl-{4-[2,2,2-trifluoro-1-hydroxy-1-(trifluoromethyl)ethyl]phenyl}propanoate in tetrahydrofuran can be added an equivalent amount of 1,5-diazabicyclo[3.4.0]nonene-5. The resulting reaction mixture can be stirred at elevated temperature until thin layer chromatographic analysis of a reaction sample indicates the reaction to be complete. The solvent can be removed and the residual oil dissolved in ether to obtain an ether solution which can be extracted with 1N hydrochloride acid and then by 2N sodium hydroxide solution. The resulting sodium hydroxide solution can be heated on the steam bath, cooled and made acidic with concentrated hydrochloric acid to obtain a product which can be isolated from the aqueous phase with ether. The resulting ether solution can be dried with anhydrous magnesium sulfate, filtered, and evaporated to give 3-methyl-3-{4-[2,2,2-trifluoro-1-hydroxy-1-(trifluoromethyl)ethyl]phenyl}-2-propenoic acid.

EXAMPLES 15–17

The procedure of Example 14 can be used with the appropriate substituted ester to give the products listed in Table 3.

TABLE 3

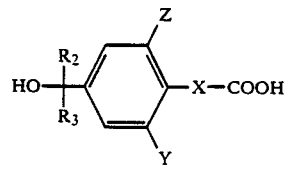

| Ex. | $R_2$ | $R_3$ | X |
|---|---|---|---|
| 15 | $HCF_2$ | $CF_3$ | $-C(CH_3)=CH-$ |
| 16 | $HCF_2$ | $HCF_2$ | $-C(CH_3)=CH-$ |
| 17 | $ClCF_2$ | $ClCF_2$ | $-C(CH_3)=CH-$ |

EXAMPLE 18

2-Nitro-4-[2,2,2-trifluoro-1-hydroxy-1-(trifluoromethyl)ethyl]benzenepropanoic Acid To a solution of 63.2 g (0.20 mole) of 4-[2,2,2-trifluoro-1-hydroxy-1-(trifluoromethyl)ethyl]benzenepropanoic acid in 160 ml of concentrated sulfuric acid is added 40 ml of fuming nitric acid (90%) dropwise with stirring at 0°–5°. Following the nitric acid addition the solution is allowed to warm to 20° with stirring over a 1-hour period. The solution is then added to a mixture of ice and water and allowed to stand for 18 hours. A precipitate results and is filtered, washed with water and dissolved in ether to obtain a solution which is washed with water, dried with anhydrous magnesium sulfate, filtered, and evaporated to give a residual solid. The residual solid is recrystallized from chlorobutane to give 40 g of 2-nitro-4-[2,2,2-trifluoro-1-hydroxy-1-(trifluoromethyl)ethyl]benzenepropanoic acid having a melting point of 115°–116°.

EXAMPLES 19–23

The procedure of Example 18 can be used with the appropriate aralkyl acid to give the compounds listed in Tables 4a and 4b.

TABLE 4a

| Ex. | $R_2$ | $R_3$ | X | Y | Z |
|---|---|---|---|---|---|
| 19 | $CF_3$ | $CF_3$ | $-CH_2-$ | $NO_2$ | H |
|  |  |  |  | m.p. 172–174° | |
| 20 | $CF_3$ | $CF_3$ | $-CH_2CH_2-$ | $NO_2$ | $OCH_3$ |
|  |  |  |  | m.p. 135–137° | |
| 21 | $CF_3$ | $HCF_2$ | $-CH_2CH(CH_3)-$ | $NO_2$ | H |
| 22 | $HCF_2$ | $HCF_2$ | $-CH_2CH_2-$ | $NO_2$ | H |

TABLE 4b

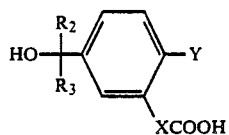

| Ex. | $R_2$ | $R_3$ | X | Y |
|---|---|---|---|---|
| 23 | $CF_3$ | $CF_3$ | $-CH_2-$ | $NO_2$ (liquid) |

EXAMPLES 24–27

The procedure of Example 14 can be used with the appropriate 2-nitro-benzenepropanoic acid ester to give the products listed in Table 5.

TABLE 5

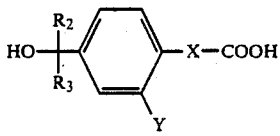

| Ex. | $R_2$ | $R_3$ | X | Y |
|---|---|---|---|---|
| 24 | $CF_3$ | $CF_3$ | $-CH=CH-$ | $NO_2$ |
| 25 | $HCF_2$ | $HCF_2$ | $-C(CH_3)=CH-$ | $NO_2$ |
| 26 | $HCF_2$ | $CF_3$ | $-CH=C(CH_3)-$ | $NO_2$ |
| 27 | $ClCF_2$ | $ClCF_2$ | $-CH=CH-$ | $NO_2$ |

EXAMPLE 28

2-Amino-4-[2,2,2-trifluoro-1-hydroxy-1-(trifluoromethyl)ethyl]benzeneacetic acid hydrochloride 2-Nitro-4-[2,2,2-trifluoro-1-hydroxy-1-(trifluoromethyl)ethyl]benzeneacetic acid (3.47 g; 0.01 mole) is dissolved in a solution 2.0 g (0.014 mole) of potassium carbonate in 200 ml of water. The solution is hydrogenated in the presence of one teaspoon of W-6 Raney Nickel at 3 atm. of hydrogen in a Parr shaker apparatus. When the reaction is complete, the catalyst is filtered off, and the filtrate is converted to the hydrochloride salt by ion exchange chromatography. The water is removed by lyophilization to give a syrupy residue of 2-amino-4-[2,2,2-trifluoro-1-hydroxy-1-(trifluoromethyl)ethyl]benzeneacetic acid hydrochloride. The structure of the product is proved by cyclizing a portion to the lactam, 1,3-dihydro-6-[2,2,2-trifluoro-1-hydroxy-1-(trifluoromethyl)ethyl]-2H-indole-2-one, m.p. 213°–225°, ir 1690 cm$^{-1}$ (—CO—) by boiling in 6N HCl, filtering off the precipitate, and recrystallizing from toluene.

EXAMPLES 29–31

The procedure of Example 28 can be used to prepare the amino aralkyl acids listed in Tables 6a and 6b from appropriate nitro aralkyl acids.

TABLE 6a

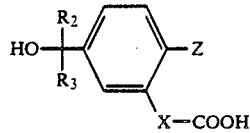

| Ex. | $R_2$ | $R_3$ | X | Z |
|---|---|---|---|---|
| 29 | $CF_3$ | $CF_3$ | $-CH_2-$ | $NH_2.HCl$ |

TABLE 6b

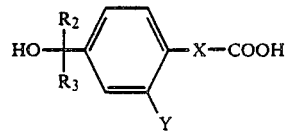

| Ex. | $R_2$ | $R_3$ | X | Y |
|---|---|---|---|---|
| 30 | $CF_3$ | $CF_3$ | $-CH_2CH_2-$ | $NH_2.HCl$ |
| 31 | $CF_3$ | $HCF_2$ | $-CH_2CH(CH_3)-$ | $NH_2.HCl$ |

EXAMPLE 32

3-{2-(N,N-Dimethylamino)-4-[2,2,2-trifluoro-1-hydroxy-1-trifluoromethyl)ethyl]benzene}propanoic Acid This compound can be obtained by the following preparation:

To a stirred mixture of 1.76 g (0.005 mole) of 3-{2-amino-4-[2,2,2-trifluoro-1-hydroxy-1-(trifluoromethyl)ethyl]benzene}propanoic acid hydrochloric, 4 ml (0.05 mole) of 37% aqueous formaldehyde, 20 ml of acetonitrile, and 0.41 g (0.005 mole) of sodium acetate is added 0.95 g (0.015 mole) of sodium cyanoborohydride. Glacial acetic acid (0.5 ml) is added over 10 minutes, and the reaction is stirred at room temperature for 2 hours. An additional 0.5 ml of glacial acetic acid is added, and the stirring is continued for 30 minutes. The reaction mixture is distributed between ether and water. The ether layer is separated, washed (saturated sodium chloride solution), dried (MgSO$_4$), and evaporated. The residue is purified by chromatography to give 3-{2-(N,N-dimethylamino)-4-[2,2,2-trifluoro-1-hydroxy-1-(trifluoromethyl)ethyl]benzene}propanoic acid.

EXAMPLES 33–37

The chloro compounds can be prepared from the corresponding amines by the method of Org. Syn. Coll. Vol. I, p. 162 while the bromo compounds can be prepared similarly by the method of Org. Syn. Coll. Vol. III, p. 185. The compounds are isolated by filtration or extraction from the aqueous reaction mixture.

TABLE 7a

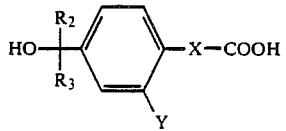

| Ex. | $R_2$ | $R_3$ | X | Y |
|---|---|---|---|---|
| 33 | $CF_3$ | $CF_3$ | $-CH_2-$ | Cl |
| 34 | $CF_3$ | $CF_3$ | $-CH_2-$ | Br |
| 35 | $CF_3$ | $CF_3$ | $-CH_2CH_2-$ | Cl |

TABLE 7a-continued

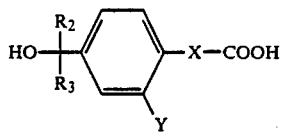

| Ex. | $R_2$ | $R_3$ | X | Y |
|---|---|---|---|---|
| 36 | $CF_3$ | $HCF_2$ | $-CH_2CH_2-$ | Br |

TABLE 7b

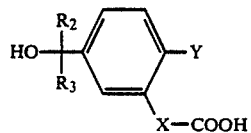

| Ex. | $R_2$ | $R_3$ | X | Y |
|---|---|---|---|---|
| 37 | $CF_3$ | $CF_3$ | $-CH_2-$ | Cl |

EXAMPLE 38

2-Methylthio-4-[2,2,2-trifluoro-1-hydroxy-1-(trifluoromethyl)ethyl]benzenepropanoic Acid This compound can be obtained by the following preparation:

A: 3,4-Dihydro-7-[2,2,2-trifluoro-1-hydroxy-1-(trifluoromethyl)ethyl]-2H-1-benzothiapyran-2-one To excess chlorosulfonic acid cooled with an ice-acetone bath can be added methyl 4-[2,2,2-trifluoro-1-hydroxy-1-(trifluoromethyl)ethyl]benzenepropanoate with stirring. The solution should be stirred for several hours. Addition of the reaction mixture to ice and isolation of the product will give 2-chlorosulfonyl-4-[2,2,2-trifluoro-1-hydroxy-1-(trifluoromethyl)ethyl]benzenepropanoic acid, methyl ester. Reduction of 2-chlorosulfonyl-4-[2,2,2-trifluoro-1-hydroxy-1-(trifluoromethyl)ethyl]benzenepropanoic acid, methyl ester with zinc in acetic acid followed by isolation of the product will give 2-mercapto-4-[2,2,2-trifluoro-1-hydroxy-1-(trifluoromethyl)ethyl]benzenepropanoic acid, methyl ester.

Heating 2-mercapto-4-[2,2,2-trifluoro-1-hydroxy-1-(trifluoromethyl)ethyl]benzenepropanoic acid, ethyl ester with p-toluenesulfonic acid in toluene at reflux will give 3,4-dihydro-7-[2,2,2-trifluoro-1-hydroxy-1-(trifluoromethyl)ethyl]-2H-1-benzothiapyran-2-one.

B: 2-Methylthio-4-[2,2,2-trifluoro-1-hydroxy-1-(trifluoromethyl)ethyl]benzenepropanoic Acid To a solution of 3,4-dihydro-7-[2,2,2-trifluoro-1-hydroxy-1-(trifluoromethyl)ethyl]-2H-1-benzothiapyran-2-one in dimethylacetamide can be added a one molar excess of sodium hydroxide in methanol. The resulting solution should be heated, and a one molar excess of methyl iodide should be added with stirring. From the resulting reaction mixture can be isolated 2-methylthio-4-[2,2,2-trifluoro-1-hydroxy-1-(trifluoromethyl)ethyl]benzenepropanoic acid, methyl ester. This ester should be dissolved in an aqueous solution of sodium hydroxide to obtain a solution which will be heated on a steam bath. Concentrated hydrochloric acid can then be added to this solution, thereby yielding a precipitate which can be isolated to give 2-methylthio-4-[2,2,2-trifluoro-1-hydroxy-1-(trifluoromethyl)ethyl]benzenepropanoic acid.

EXAMPLES 39–42

The procedure of Example 38 can be used with the appropriate aralkyl ester to give a benzothiapyran-2-one which can be reacted with the appropriate alkyl halide to give products listed in Table 8.

TABLE 8

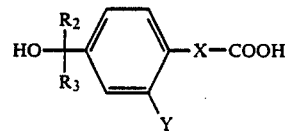

| Ex. | $R_2$ | $R_3$ | X | Y |
|---|---|---|---|---|
| 39 | $CF_3$ | $CF_3$ | $-CH_2CH_2-$ | $SC_2H_5$ |
| 40 | $HCF_2$ | $HCF_2$ | $-CH_2CH_2-$ | $SCH_3$ |
| 41 | $HCF_2$ | $CF_3$ | $-CH_2CH_2-$ | $SCH_3$ |
| 42 | $CF_3$ | $CF_3$ | $-CH_2CH(CH_3)-$ | $SC_3H_7$ |

EXAMPLE 43

3-{2-Methoxy-4-[2,2,2-trifluoro-1-hydroxy-1-(trifluoromethyl)ethyl]phenyl}-2-propenoic Acid A: 1-Methoxy-3-[2,2,2-trifluoro-1-hydroxy-1-(trifluoromethyl)ethyl]benzene To a suspension of 13.5 g (0.55 g atoms) of sublimed magnesium chips in 25 ml of anhydrous tetrahydrofuran in a reaction flask fitted with a water-cooled condenser are added 10 g (0.05 mole) of 3-bromo-1-methoxybenzene and 0.5 ml of 1,2-dibromoethane. The resulting reaction mixture is stirred and heated gently until a reaction is initiated. To the stirred reaction mixture is added dropwise a solution of 90 g (0.48 mole) of 3-bromo-1-methoxybenzene in 250 ml of anhydrous tetrahydrofuran at such a rate that gentle reflux is maintained. The reaction mixture is stirred for an additional two hours. The resulting solution is then cooled to 0° and the reaction flask is fitted with a jacketed dropping funnel topped by a dry ice condenser. The water condenser is replaced by an additional dry ice condenser. To the jacketed dropping funnel are added 85 g (50 ml) (0.55 mole) of condensed hexafluoroacetone. The condensed hexafluoroacetone is added dropwise to the stirred solution which is cooled to 0° to −10° with an ice-acetone bath. When the addition of the hexafluoroacetone is complete, the resulting solution is allowed to warm to 20°–25° and stirring is continued for an additional 18 hours. The solution is cooled to 0° and treated with 6N hydrochloric acid to obtain an acidic solution to which is added 1-liter of ether. The resulting ether layer is washed with water, washed with a 5% sodium bicarbonate solution, dried with anhydrous magnesium sulfate, filtered and evaporated at reduced pressure to yield a residual solid which is recrystallized from chlorobutane to give 78 g of 1-methoxy-3-[2,2,2-trifluoro-1-hydroxy-1-(trifluoromethyl)ethyl]benzene.

B: 2-Methoxy-4-[2,2,2-trifluoro-1-hydroxy-1-(trifluoromethyl)ethyl]benzaldehyde

To a solution of 31.6 g (0.12 mole) of 1-methoxy-3-[2,2,2-trifluoro-1-hydroxy-1-(trifluoromethyl)ethyl]benzene in 200 ml dichloromethane is added 38 g (0.2 mole) of titanium tetrachloride at 0°–5° with stirring under a nitrogen atmosphere. After the resulting solution is stirred for 15 minutes, 11.5 g (0.1 mole) of α,α- dichloromethyl methyl ether is added dropwise at 0°–5° C. Stirring is continued while the temperature of the solution is allowed to reach 20°–25° during 18 hours. The solution is then added with stirring to a solution of 100 ml 6N hydrochloric acid in 500 ml of ice and water. The resulting organic phase is separated leaving an aqueous phase which is washed with three 300 ml portions of dichloromethane. The combined dichloromethane extracts are washed with 1N hydrochloric acid and then with saturated sodium chloride solution. The dichloromethane solution is dried with anhydrous magnesium sulfate, filtered, and evaporated at reduced pressure to obtain an oily solid which is triturated with chlorobutane, filtered and recrystallized from chlorobutane to give 14.5 g of 2-methoxy-4-[2,2,2-trifluoro-1-hydroxy-(trifluoromethyl)ethyl]benzaldehyde having a melting point of 144°–146°.

C: 3-{2-Methoxy-4-[2,2,2-trifluoro-1-hydroxy-1-(trifluoromethyl)ethyl]phenyl}-2-propenoic Acid To a solution of 15 g (0.05 mole) 2-methoxy-4-[2,2,2-trifluoro-1-hydroxy-1-(trifluoromethyl)ethyl]benzaldehyde in 50 ml of pyridine are added 11 g (0.11 mole) of malonic acid and 1 g of piperidine. The solution is stirred and gradually heated to 80°. Heating and stirring are continued for 1 hour at 80°. The solution is then heated at reflux for an additional 3 hours, cooled, and evaporated at reduced pressure to obtain a residual oil which is extracted into ether. The resulting ether solution is washed with water and 1N hydrochloric acid, dried with anhydrous magnesium sulfate, filtered, and evaporated at reduced pressure to obtain a residual solid which is recrystallized from chlorobutane/hexane mixed solvent to give 10.5 g of 3-{2 -methoxy-4-[2,2,2-trifluoro-1-hydroxy-1-(trifluoromethyl)ethyl]phenyl}-2-propenoic acid having a melting point of 138°–140°.

EXAMPLES 44–48

The procedures of Example 43 can be used with the appropriate starting materials to give the products listed in Table 9.

TABLE 9

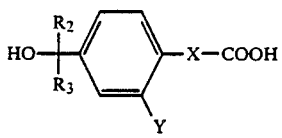

| Ex. | R₂ | R₃ | X | Y |
|---|---|---|---|---|
| 44 | CF₃ | CF₃ | —CH=CH— | OC₂H₅ |
| 45 | CF₃ | CF₃ | —CH=CH— | OC₃H₇ |
| 46 | HCF₂ | HCF₂ | —CH=CH— | OCH₃ |
| 47 | HCF₂ | CF₃ | —CH=CH— | OC₂H₅ |
| 48 | ClCF₂ | ClCF₂ | —CH=CH— | OC₂H₅ |
| 49 | ClCF₂ | ClCF₂ | —CH=CH— | OCH₃ |

EXAMPLE 50

3-{2-Methoxy-5-[2,2,2-trifluoro-1-hydroxy-1-(trifluoromethyl)ethyl]phenyl}-2-propenoic Acid A: Methoxy-5-[2,2,2-trifluoro-1-hydroxy-1-(trifluoromethyl)ethyl]benzaldehyde This compound is prepared as described in Example 43 using 1-methoxy-4-[2,2,2-trifluoro-1-hydroxy-1-(trifluoromethyl)ethyl]benzene [B. S. Farah, et al., *J. Org. Chem.*, 30, 1003 (1965)] in place of 1-methoxy-3-[2,2,2-trifluoro-1-hydroxy-1-(trifluoromethyl)ethyl]benzene.

The product is recrystallized from 1-chlorobutane to give crystals, m.p. 160°–161°, in 33% yield.

B: 3-{2-Methoxy-5-[2,2,2-trifluoro-1-hydroxy-1-(trifluoromethyl)ethyl]phenyl}-2-propenoic Acid This compound is prepared as described in Example 43 using 2-methoxy-5-[2,2,2-trifluoro-1-hydroxy-1-(trifluoromethyl)ethyl]benzaldehyde in place of 2-methoxy-4-[2,2,2-trifluoro-1-hydroxy-1-(trifluoromethyl)ethyl]benzaldehyde. There is obtained after recrystallization from 1-chlorobutane the product 3-{2-methoxy-5-[2,2,2-trifluoro-1-hydroxy-1-(trifluoromethyl)ethyl]phenyl}-2-propenoic acid, m.p. 184°–186°, in 84% yield. The infrared spectrum is consistent with the structure.

EXAMPLES 50–54

The alkyl-substituted 4-(2,2,2-trifluoro-1-hydroxy-1-(trifluoromethyl)ethyl]benzenealkenoic acids listed in Tables 10a and 10b can be prepared by the procedure of Example 43 using the appropriate bromoalkylbenzenes. In Examples 53 and 54, the intermediate 1-alkyl-4-[2,2,2-trifluoro-1-hydroxy-1-(trifluoromethyl)-ethyl]-benzenes can be prepared by the method of B. S. Farah, et al., *J. Org. Chem.*, 30, 998 (1965).

TABLE 10a

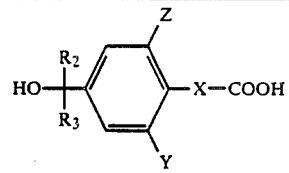

| Ex. | R₂ | R₃ | X | Y | Z |
|---|---|---|---|---|---|
| 50 | CF₃ | CF₃ | —CH=CH— | CH₃ | H |
| 51 | CF₃ | CF₃ | —CH=CH— | (CH₂)₂CH₃ | H |
| 52 | CF₃ | CF₃ | —CH=CH— | CH₃ | CH₃ |

TABLE 10b

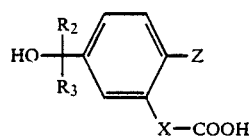

| Ex. | R₂ | R₃ | X | Z |
|---|---|---|---|---|
| 53 | CF₃ | CF₃ | —CH=CH— | CH₃ |
| 54 | CF₃ | CF₃ | —CH=CH— | (CH₂)₃CH₃ |

The substituted alkylbenzene intermediates to the compounds of Examples 53 and 54 can be prepared by the method of B. S. Farah, et al., *J. Org. Chem.*, 30 998 (1965).

EXAMPLE 55

2-Methoxy-4-[2,2,2-trifluoro-1-hydroxy-1-(trifluoromethyl)ethyl]benzenepropanoic Acid To 100 ml of ethanol are added 8.8 g (0.025 mole) of 3-{2-methoxy-4-[2,2,2-trifluoro-1-hydroxy-1-(trifluoromethyl)ethyl]phenyl}-2-propenoic acid to produce a solution which is added to a pressure bottle and flushed with nitrogen. To the solution is added 1 g of 10% palladium on carbon. The pressure bottle is placed in a hydrogenation apparatus and pressurized to 1384 g/cm² (50 lbs/in.²) with hydrogen. The pressure bottle is shaken until the pressure ceases dropping. The resulting solution is vented, filtered and evaporated at reduced pressure to obtain a residual solid which is recrystallized from chlorobutane o give 7.0 gm of 2-methoxy-4-[2,2,2-trifluoro-1-hydroxy-1-(trifluoromethyl)ethyl]benzenepropanoic acid having a melting point of 116°-117°.

EXAMPLES 56-66

The procedure of Example 55 can be used with the appropriate 2-alkyl- or 2-alkoxy-phenylpropenoic acid to give the products listed in Tables 11a and 11b.

TABLE 11a

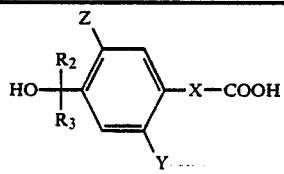

| Ex. | $R_2$ | $R_3$ | X | Y | Z |
|---|---|---|---|---|---|
| 56 | $CF_3$ | $CF_3$ | —$CH_2CH_2$— | $OC_2H_5$ | H |
| 57 | $CF_3$ | $CF_3$ | —$CH_2CH_2$— | $OC_3H_7$ | H |
| 58 | $CF_3$ | $CF_3$ | —$CH_2CH(CH_3)$— | $OCH_3$ | H |
| 59 | $HCF_2$ | $CF_3$ | —$CH_2CH_2$— | $OCH_3$ | H |
| 60 | $HCF_2$ | $HCF_2$ | —$CH_2CH_2$— | $OC_2H_5$ | H |
| 61 | $CF_3$ | $CF_3$ | —$CH_2CH_2$— | H | $OCH_3$ |
|    |        |        |              | m.p. 112-114° C. | |
| 62 | $CF_3$ | $CF_3$ | —$CH_2CH_2$— | $CH_3$ | H |
| 63 | $CF_3$ | $CF_3$ | —$CH_2CH_2$— | $(CH_2)_2CH_3$ | H |

TABLE 11b

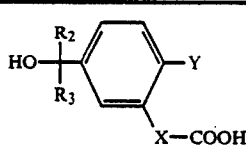

| Ex. | $R_2$ | $R_3$ | X | Y |
|---|---|---|---|---|
| 64 | $CF_3$ | $CF_3$ | —$CH_2CH_2$— | $OCH_3$ |
|    |        |        | m.p. 131-132° C. | |
| 65 | $CF_3$ | $CF_3$ | —$CH_2CH_2$— | $CH_3$ |
| 66 | $CF_3$ | $CF_3$ | —$CH_2CH_2$— | —$(CH_2)_3CH_3$ |

EXAMPLE 67

2-Methoxy-4-[2,2,2-trifluoro-1-hydroxy-1-(trifluoromethyl)ethyl]benzeneacetic Acid To a solution of 20 g (0.066 mole) of 2-methoxy-4-[2,2,2-trifluoro-1-hydroxy-1-(trifluoromethyl)ethyl]-benzaldehyde in 100 ml of anhydrous tetrahydrofuran are added 10 g (0.071 mole) of methyl methylthiomethyl sulfoxide and 50 ml of a 40% solution of benzyltrimethylammonium hydroxide in methanol. The resulting solution is stirred and heated at reflux for 96 hours. The solution is then concentrated at reduced pressure to obtain a residual oil which is next added to 50 ml of water and neutralized with 6N hydrochloric acid. The resultant mixture is extracted with ether, dried with anhydrous magnesium sulfate, filtered and evaporated at reduced pressure to give a residual oil which is purified by high pressure liquid chromatography to give 16 g of an oil shown to be homogeneous by thin-layer chromatography. The oil is added to a solution of 100 ml 6N hydrochloric acid in 100 ml dimethoxyethane to obtain a solution which is then stirred and heated at reflux for 20 hours. The solution is concentrated at reduced pressure to give a residual oil which is dissolved in 100 ml of 1N sodium hydroxide solution. The solution is heated to 60° for 1 hour, neutralized with 1N hydrochloric acid and extracted with ether to obtain an ether solution which is dried with anhydrous magnesium sulfate, filtered and evaporated at reduced pressure to give a residual solid. This residual solid is recrystallized from chlorobutane to give 10.2 g of 2-methoxy-4-[2,2,2-trifluoro-1-hydroxy-1-(trifluoromethyl)ethyl]benzeneacetic acid having a melting point of 133°-135°.

EXAMPLE 68

3-[2,2,2-Trifluoro-1-hydroxy-1-(trifluoromethyl)ethyl]-benzeneacetic acid and

4-[2,2,2-trifluoro-1-hydroxy-1-(trifluoromethyl)ethyl]-benzeneacetic Acid

Methyl phenylacetate (450 g), 500 ml of dichloromethane, 480 g of anhydrous aluminum chloride, and 498 g of hexafluoroacetone are agitated for 16 hours (use of a shaker bomb is convenient). The mixture is poured into a mixture of ice and concentrated hydrochloric acid. The dichloromethane layer is separated, washed (1N HCl), dried ($MgSO_4$), and evaporated to give 795 g of residue. Distillation gives 757 g (80%) of a liquid, b.p. 144 (9 mm), which consists of a mixture of the methyl esters of 3- and 4-[2,2,2-trifluoro-1-hydroxy-1-(trifluoromethyl)ethyl]benzeneacetic acid.

A 51.4 g portion of the mixture of methyl esters is refluxed in a mixture of 50 ml of acetic acid, 50 ml of water, and 50 ml of concentrated sulfuric acid for 16 hours. The cooled reaction mixture is poured into ice-water and extracted with ether. The ether solution is washed (water, then saturated sodium chloride solution), dried ($MgSO_4$), and evaporated to give 49.5 g of crude residue. Crystallization from carbon tetrachloride gives 15.3 g (32%) of crystalline 3-[2,2,2-trifluoro-1-hydroxy-1-(trifluoromethyl)ethyl]benzeneacetic acid, m.p. 125°-126.5°, with a complex aromatic absorption band in the nmr spectrum at δ7.2-7.8 ppm ($d_6DMSO$). A second crop of 19.7 g, m.p. 76°-82°, is obtained. This is recrystallized again from carbon tetrachloride and then from toluene to give 4.4 g of crystals, m.p. 81.5°-84°, identified as 4-[2,2,2-trifluoro-1-hydroxy-1-(trifluoromethyl)ethyl]benzeneacetic acid by the NMR spectrum, which shows the typical aromatic $A_2B_2$ pattern centered at δ7.37 ppm.

EXAMPLES 69-75

The procedure of Example 67 can be used with the appropriate 2-alkoxy- or 2-alkylbenzaldehyde to give the products listed in Tables 12a and 12b.

TABLE 12a

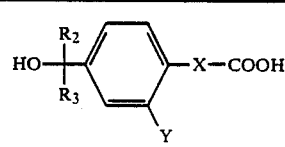

| Ex. | $R_2$ | $R_3$ | X | Y |
|---|---|---|---|---|
| 69 | $CF_3$ | $CF_3$ | —$CH_2$— | $OC_2H_5$ |
| 70 | $HCF_2$ | $HCF_2$ | —$CH_2$— | $OCH_3$ |
| 71 | $HCF_2$ | $CF_3$ | —$CH_2$— | $OCH_3$ |
| 72 | $CF_3$ | $CF_3$ | —$CH_2$— | $CH_3$ |

TABLE 12b

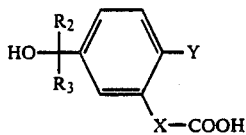

| Ex. | $R_2$ | $R_3$ | X | Y |
|---|---|---|---|---|
| 73 | $CF_3$ | $CF_3$ | $-CH_2-$ | $OCH_3$ |
| 74 | $CF_3$ | $CF_3$ | $-CH_2-$ | $CH_3$ |
| 75 | $CF_3$ | $CF_3$ | $-CH_2-$ | $(CH_2)_3CH_3$ |

EXAMPLE 76

Methyl 2-Methoxy-4-[2,2,2-trifluoro-1-hydroxy-1-(trifluoromethyl)ethyl]benzenepropanoate To a solution of 50 ml of methanol in 50 ml toluene are added 7.0 g (0.02 mole) of 2-methoxy-4-[2,2,2-trifluoro-1-hydroxy-1-(trifluoromethyl)ethyl]benzenepropanoic acid and 1 ml of concentrated sulfuric acid. The resulting solution is stirred, heated at reflux for 18 hours, then concentrated to 20 ml at reduced pressure, and extracted with ether. The resulting ether solution is washed with 5% sodium bicarbonate solution and water. The solution is dried with anhydrous magnesium sulfate, filtered and concentrated at reduced pressure to obtain a residual solid which is recrystallized from petroleum ether to give 5.5 g of methyl 2-methoxy-4-[2,2,2-trifluoro-1-hydroxy-1-(trifluoromethyl)ethyl]benzenepropanoate having a melting point of 78°-80°.

EXAMPLES 77-89

The procedure of Example 76 can be used with the appropriate aralkyl acid and alcohol to give the products listed in Table 13.

EXAMPLE 90

2-Methoxy-4-[2,2,2-trifluoro-1-hydroxy-1-(trifluoromethyl)ethyl]benzenepropanoic Acid, (4-Methoxyphenyl) Ester To a solution of 16 g (0.046 mole) of 2-methoxy-4-[2,2,2-trifluoro-1-hydroxy-1-(trifluoromethyl)ethyl]benzenepropanoic acid in 300 ml of toluene are added 8 gm (0.060 mole) of oxalyl chloride and 3 drops of dimethylformamide. After evolution of hydrogen chloride ceases, the resulting reaction mixture is heated at reflux for 2 hours to obtain a solution which is cooled and concentrated at reduced pressure to give 2-methoxy-4-[2,2,2-trifluoro-1-hydroxy-1-(trifluoromethyl)ethyl]benzenepropanoyl chloride.

A solution of 5 g (0.02 mole) of 2-methoxy-4-[2,2,2-trifluoro-1-hydroxy-1-(trifluoromethyl)ethyl]benzenepropanoyl chloride in 100 ml of toluene is added to a solution of 2.5 g (0.02 mole) of p-methoxyphenol and 3 g (0.03 mole) of triethylamine in 50 ml of toluene. The resulting solution is stirred and heated at reflux for 4 hours. The solution is then cooled and evaporated at reduced pressure to obtain a residual oil which is extracted with ether. The resulting ether solution is washed with 2N hydrochloric acid and 5% sodium bicarbonate solution, and dried with anhydrous magnesium sulfate. The resulting dried solution is filtered and concentrated at reduced pressure to yield a residual oil which is chromatographed on silica ( Silicar ® CC-7 silica manufactured by Mallinckrodt, Inc.). Elution with toluene gives, after concentration, 2-methoxy-4-[2,2,2-trifluoro-1-hydroxy-1-(trifluoromethyl)ethyl]benzenepropanoic acid, (4-methoxyphenyl) ester as a clear homogeneous oil. The formation of the ester is confirmed by the presence of an ester carbonyl band at 5.79µ.

EXAMPLES 91-101

The procedure of Example 90 can be used with the appropriate aralkyl acid and alcohol or thiol to give the products listed in Table 14.

TABLE 13

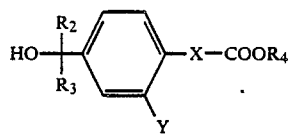

| Ex. | $R_2$ | $R_3$ | X | Y | $R_4$ |
|---|---|---|---|---|---|
| 77 | $CF_3$ | $CF_3$ | $-CH_2CH_2-$ | $OCH_3$ | $OC_2H_5$ m.p. 55-57° |
| 78 | $CF_3$ | $CF_3$ | $-CH_2-$ | $OCH_3$ | $OCH_3$ m.p. 81-83° |
| 79 | $CF_3$ | $CF_3$ | $-CH_2CH_2-$ | $OCH_3$ | $OC_4H_9$ |
| 80 | $CF_3$ | $CF_3$ | $-CH_2CH_2-$ | $OC_2H_5$ | $OCH_2CH=CH_2$ |
| 81 | $CF_3$ | $CF_3$ | $-CH_2CH(CH_3)-$ | $OCH_3$ | $O(CH_2)_8CH=CH_2$ |
| 82 | $HCF_2$ | $CF_3$ | $-CH_2CH_2-$ | $OCH_3$ | $OC_3H_7$ |
| 83 | $HCF_2$ | $HCF_2$ | $-CH_2CH_2-$ | $OC_2H_5$ | $OCH_3$ |
| 84 | $ClCF_2$ | $ClCF_2$ | $-CH_2CH_2-$ | $OCH_3$ | $OCH_3$ |
| 85 | $HCF_2$ | $HCF_2$ | $-CH_2-$ | $OCH_3$ | $OC_2H_5$ |
| 86 | $HCF_2$ | $CF_3$ | $-CH_2CH(CH_3)-$ | $OCH_3$ | $O(CH_2)_9CH_3$ |
| 87 | $CF_3$ | $CF_3$ | $-CH_2CH_2-$ | $OC_3H_7$ | $OC_3H_7$ |
| 88 | $CF_3$ | $CF_3$ | $-CH=CH-$ | $OCH_3$ | $OCH_3$ |
| 89 | $CF_3$ | $CF_3$ | $-CH=C(CH_3)-$ | $OC_2H_5$ | $OC_2H_5$ |

TABLE 14

Structure:
$$HO-C(R_2)(R_3)-\text{C}_6\text{H}_3(Y)-X-COR_4$$

| Ex. | $R_2$ | $R_3$ | X | Y | $R_4$ |
|---|---|---|---|---|---|
| 91 | $CF_3$ | $CF_3$ | $-CH_2CH_2-$ | $OCH_3$ | 4-($OCH_3$)-$C_6H_4$-$OCH_2$— oil |
| 92 | $CF_3$ | $CF_3$ | $-CH_2CH_2-$ | $OCH_3$ | $C_6H_5$-$CH_2CH_2O$— oil |
| 93 | $CF_3$ | $CF_3$ | $-CH_2CH_2-$ | $OC_2H_5$ | $SCH_3$ |
| 94 | $HCF_2$ | $CF_3$ | $-CH_2CH_2-$ | $OC_2H_5$ | 3-Cl-4-$OCH_3$-$C_6H_3$-O— |
| 95 | $HCF_2$ | $HCF_2$ | $-CH_2CH_2-$ | $OCH_3$ | 4-$CF_3$-$C_6H_4$-$OCH_2$— |
| 96 | $CF_3$ | $CF_3$ | $-CH_2CH_2-$ | H | $OC_2H_5$ b.p. 180–185° (0.5 mm/Hg) |
| 97 | $CF_3$ | $CF_3$ | $-CH_2CH_2-$ | $NO_2$ | 4-$COOC_2H_5$-$C_6H_4$-O— |
| 98 | $CF_3$ | $CF_3$ | $-CH_2CH_2-$ | $SCH_3$ | 4-$CH_3$-$C_6H_4$-O— |
| 99 | $CF_3$ | $CF_3$ | $-CH_2CH_2-$ | $NO_2$ | $SC_{10}H_{21}(\underline{n})$ |
| 100 | $CF_3$ | $CF_3$ | $-CH_2CH_2-$ | $SCH_3$ | $S(CH_2)_8CH=CH_2$ |
| 101 | $CF_3$ | $CF_3$ | $-CH=CH-$ | $OCH_3$ | 2-Br-4-$NO_2$-$C_6H_3$-O— |

EXAMPLES 102-109

The procedure of Example 90 can be used with the appropriate aralkyl acid and with dimethylamine in place of an alcohol and triethylamine to yield the N,N-dimethylamides listed in Table 15.

TABLE 15

Structure:
$$HO-C(R_2)(R_3)-\text{C}_6\text{H}_3(Y)-X-COR_4$$

| Ex. | $R_2$ | $R_3$ | X | Y | $R_4$ |
|---|---|---|---|---|---|
| 102 | $CF_3$ | $CF_3$ | $-CH_2CH_2-$ | H | $N(CH_3)_2$ m.p. 117–119° |
| 103 | $CF_3$ | $CF_3$ | $-CH_2CH_2-$ | $NO_2$ | $N(CH_3)_2$ m.p. 163–165° |
| 104 | $CF_3$ | $CF_3$ | $-CH=CH-$ | $OCH_3$ | $N(CH_3)_2$ |
| 105 | $CF_3$ | $CF_3$ | $-CH(CH_3)CH_2-$ | H | $N(CH_3)_2$ |

TABLE 15-continued

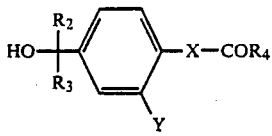

| Ex. | $R_2$ | $R_3$ | X | Y | $R_4$ |
|---|---|---|---|---|---|
| 106 | $CF_3$ | $CF_3$ | $-CH_2CH(CH_3)-$ | H | $N(CH_3)_2$ m.p. 104–106° |
| 107 | $CF_3$ | $CF_3$ | $-CH_2CH_2-$ | $OCH_3$ | $N(CH_3)_2$ m.p. 144–145° |
| 108 | $HCF_2$ | $HCF_2$ | $-CH_2CH_2-$ | $OC_2H_5$ | $N(CH_3)_2$ |
| 109 | $HCF_2$ | $CF_3$ | $-CH_2CH_2-$ | $SCH_3$ | $N(CH_3)_2$ |

EXAMPLE 110

3-{2-Nitro-4-[2,2,2-trifluoro-1-methoxy-1-(trifluoromethyl)ethyl]phenyl}-N,N-dimethylpropanamide To a suspension of 2.15 (0.085 mole) of sodium hydride in 200 ml dimethylformamide is added 29.1 g (0.075 mole) of 3-{2-nitro-4-[2,2,2-trifluoro-1-hydroxy-1-(trifluoromethyl)ethyl]phenyl}-N,N-dimethylpropanamide in in 50 ml dimethylformamide at such a rate that excessive foaming is avoided. To the resulting suspension, stirred in a nitrogen atmosphere, is added 14.2 g (0.10 mole) of methyl iodide to give a reaction mixture, which is stirred at room temperature overnight. The reaction mixture is then treated with 5 ml of ethanol, poured into 1-liter of water and extracted with ether. The resulting ether solution is washed with water, dried over anhydrous magnesium sulfate, filtered and evaporated at reduced pressure to obtain a residual oil which is chromatographed on Silicar ® CC-7. Elution with chloroform gives a major fraction consisting of 16 g which is recrystallized from hexane to give 3-{2-nitro-4-[2,2,2-trifluoro-1-methoxy-1-(trifluoromethyl)ethyl]phenyl}-N,N-dimethylpropanamide having a melting point of 51°–54°.

EXAMPLES 111–116

The procedure of Example 110 can be used with the appropriate aralkyl ester or dimethylamide and alkyl halide or acyl halide to give the products listed in Table 16. When substituted (1-hydroxyethyl)aralkyl acids are treated with alkyl halides as in Example 110, it is understood that the products are the corresponding substituted (1-alkoxyethyl)-aralkyl esters. The substituted (1-alkoxyethyl)aralkyl acids can be generated by basic hydrolysis of the corresponding substituted (1-alkoxyethyl)aralkyl ester.

EXAMPLE 118

3-[2,2,2-Trifluoro-1-hydroxy-1-(trifluoromethyl)ethyl]-propanoic Acid

A: 2-{3-[2,2,2-Trifluoro-1-hydroxy-1-(trifluoromethyl)ethyl]phenyl}ethanol

To one liter of 1M borane-tetrahydrofuran complex was added a solution of 100 g (0.33 mole) of 3-[2,2,2-trifluoro-1-hydroxy-1-(trifluoromethyl)ethyl]benzeneactic acid in 200 ml of tetrahydrofuran. The solution is refluxed for 16 hours under nitrogen. The solution is then refluxed with 400 ml of 6N hydrochloric acid until evolution of hydrogen is complete. The mixture is filtered and evaporated. The residue is refluxed with 500 ml of methanol containing 10 ml of concentrated hydrochloric acid until methyl borate is no longer evolved. The solution is evaporated, and the residue is distilled at 110°–115° (0.7 mm) to give 37 g of 2-{3-[2,2,2-trifluoro-1-hydroxy-1-(trifluoromethyl)ethyl]phenyl}ethanol.

B: 2-{3-[2,2,2-Trifluoro-1-hydroxy-1-(trifluoromethyl)ethyl]phenyl}ethanol methanesulfonic Acid Ester To 37 g (0.128 mole) of 2-{3-[2,2,2-trifluoro-1-hydroxy-1-(trifluoromethyl)ethyl]phenyl}ethanol in 150 ml of dichloromethane is added 15 g (0.15 mole) of triethylamine. The solution is cooled to 10° and 16 g (0.14 mole) of methanesulfonyl chloride is added. After 3 days, the solution is washed with hydrochloric acid, dried (MgSO4), and evaporated. The residue is chromatographed to give 2-{3-[2,2,2-trifluoro-1-hydroxy-1-(trifluoromethyl)phenyl}ethanol methanesulfonic acid ethyl ester, m.p. 68°–69°.

C: 3-{3-[2,2,2-Trifluoro-1-hydroxy-1-(trifluoromethyl)ethyl]phenyl}propanoic Acid To 4.00 g (0.0011 mole) of 2-{3-[2,2,2-trifluoro-1-hydroxy-1-(trifluoromethyl]ethyl}ethanol methanesulfonic acid ester in 100 ml of ethanol is added a solution of 2.00 g (0.031 mole) of potassium cyanide in 5 ml of water. The stirred mixture is refluxed for three days. The alcohol is removed by evaporation, and the residue is extracted with ether. The ether extract is washed with water and with saturated sodium chloride solution, dried (MgSO4), and evaporated to give the oily 3-{3-[2,2,2-trifluoro-1-hydroxy-1-(trifluoromethyl)ethyl]-phenyl}propionitrile, whose IR spectrum shows the presence of the nitrile band. The crude nitrile is refluxed for 5 days with 20 ml of 50% sulfuric acid. The reaction mixture is allowed to cool, diluted with water, and extracted with ether. The ether extract is evaporated, and the residue is dissolved in 100 ml of 5% NaHCO3 solution. The aqueous phase is extracted with ether, acidified, and again extracted with ether. The ether

TABLE 16

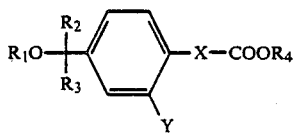

| Ex. | $R_1$ | $R_2$ | $R_3$ | X | Y | $R_4$ |
|---|---|---|---|---|---|---|
| 111 | $CH_3$ | $CF_3$ | $CF_3$ | $-CH_2CH_2-$ | $OCH_3$ | $SCH_2CH=CH_2$ |
| 112 | $C_2H_5$ | $CF_3$ | $CF_3$ | $-CH_2CH_2-$ | $OCH_3$ | $N(CH_3)_2$ |
| 113 | $CH_3CO$ | $CF_3$ | $CF_3$ | $-CH_2CH_2-$ | $OCH_3$ | $OCH_3$ |
| 114 | $C_2H_5CO$ | $HCF_2$ | $HCF_2$ | $-CH_2CH_2-$ | $OCH_3$ | $OCH_3$ |
| 115 | $C_5H_{11}CO$ | $CF_3$ | $CF_3$ | $-CH_2-$ | $NO_2$ | $OCH_3$ |
| 116 | n-$C_6H_{13}$ | $CF_3$ | $CF_3$ | $-CH_2-$ | $OCH_3$ | $N(CH_3)_2$ |
| 117 | $C_6H_5CH_2$ | $CF_3$ | $CF_3$ | $-CH_2CH_2-$ | $OCH_3$ | $OC_2H_5$ | solution is washed, dried, and evaporated. The residue is recrystallized from 1-chlorobutane to give 1.0 g of 3-{3-[2,2,2-trifluoro-1-hydroxy-1-(trifluoromethyl)ethyl]phenyl}propanoic acid, m.p. 112°-113°.

EXAMPLES 119-120

The procedure of Example 118 can be used to homologate other arylalkanoic acids to yield the products in Table 17.

TABLE 17

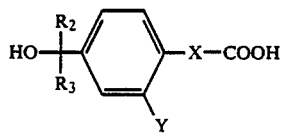

| Ex. | $R_2$ | $R_3$ | X | Y |
|-----|-------|-------|------|------|
| 119 | $CF_3$ | $CF_3$ | $-(CH_2)_3-$ | $OCH_3$ |
| 120 | $CF_3$ | $CF_3$ | $-(CH_2)_3-$ | $CH_3$ |

Dosage

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homeostatic mechanism and includes mammals and birds.

The dosage administered will will be dependent on the age, health and weight of the recipient; the extent of disease, kind of concurrent treatment, if any, frequency of treatment and the nature of the effect desired. Dosages as high as 100 milligrams per kilogram of body weight can be used. Usually, a daily dosage of active ingredient compound will be from about 0.01 to 50 milligrams per kilogram of body weight. Ordinarily, from 0.05 to 40, and preferably 0.1 to 20, milligrams per kilogram per day in one or more applications per day is effective to obtain desired results. For the more potent compounds of the invention, e.g., methyl 2-methoxy-4-[2,2,2-trifluoro-1-hydroxy-1-(trifluoromethyl)ethyl]-phenylpropanoate, the daily dosage ranges are from about 0.01 to 10 mg/kg, preferably 0.05 to 10 mg/kg, and more preferably 0.05 to 5 mg/kg.

Dosage forms (compositions) suitable for internal administration contain from about 0.1 milligrams to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules can contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 27.5 milligrams of lactose. Appropriate coatings may be applied to increase palatability or delay absorption.

Injectable

A parenteral composition suitable for administration by injection is prepared by stirring 1.5% by weight of active ingredient in 10-60% by volume of co-solvents, like propylene glycol in water. The resultant solution can be sterilized by filtration.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XV and adjusting the pH of the solution to between 6 and 7. The solution can be sterilized by filtration.

Utility

The antihypertensive activity of the compounds of this invention is evidenced by tests conducted in hypertensive rats. In these tests, rats are made hypertensive by subcutaneous implantation of pellets of desoxycorticosterone acetate (DOCA) and by giving the rats saline solution to drink essentially according to the method described by Sturtevant (Annals of Internal Medicine, 49, 1281 [1958]). Graded dose levels of each compound are administered orally to groups of 8 hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by modification of the microphone-manometer technique (Friedman, M. and Freed, S. C., Proc. Soc. Exp. Biol. and Med., 70, 670 [1949]). That dose of compound which produces a 30 mm mercury (mm Hg) reduction in blood pressure when compared to the mean systolic arterial blood pressure of the control animals is then determined (Effective Dose 30). For example, an ED30 of 0.19 mg/kg orally was obtained with the compound of Example 46. ED 30's of 0.31, 0.45 and 0.23 were obtained with the compounds of Examples 47, 36 and 60; other examples are given in Table 18.

TABLE 18
Effects on Systolic Arterial Blood Pressures of DOCA-Hypertensive Rats

| Example | ED30 mg/kg p.o. |
|---|---|
| 1 | 13 |
| 7 | 23 |
| 8 | 6.2 |
| 18 | 2.7 |
| 19 | 10 |
| 43 | 1.2 |
| 55 | 0.45 |
| 61 | 50 |
| 64 | 18 |
| 67 | 4.0 |
| 76 | 0.19 |
| 77 | 0.31 |
| 78 | 9.0 |
| 90 | 0.23 |
| 91 | 0.78 |
| 92 | 0.68 |
| 96 | 16 |
| 102 | 6.4 |
| 103 | 4.3 |
| 105 | 15 |
| 106 | 9.0 |
| 107 | 1.4 |
| 110 | 40 |
| 118 | 33 |

What is claimed is:

1. A compound of the formula:

$$R_1O-\underset{\underset{Y}{R_3}}{\overset{\overset{Z}{R_2}}{\bigcirc}}-X-COR_4 \quad \text{or} \quad R_1O-\underset{R_3}{\overset{R_2}{\bigcirc}}-\underset{X-COR_4}{\overset{Y}{\bigcirc}}$$

$$\text{I} \qquad\qquad \text{II}$$

wherein $R_1$ is H, $C_1$-$C_6$ alkyl, $C_2$-$C_{12}$ acyl, —$CH_2A$— or —$C(O)$—$A$;

$$A \text{ is } -\underset{M}{\overset{L}{\bigcirc}}$$

where

L and M are independently H, F, Cl, Br, $NO_2$, $C_1$-$C_4$ alkyl, $C_1$-$C_4$ alkoxy, $CF_3$, $OCF_3$, CN, phenyl or COOR', where R' is H, $CH_3$ or $C_2H_5$;

$R_2$ and $R_3$ are independently $CF_3$, $CF_2Cl$ or $CF_2H$;

$R_4$ is $NR_6R_7$, O—$R_5$, S—$R_5$ or Cl;

$R_5$ is H, $C_1$-$C_{10}$ alkyl, $C_3$-$C_{10}$ alkenyl, A or —$R_8$—A;

$R_6$ and $R_7$ are independently H, $C_1$-$C_6$ alkyl, A or —$R_8$—A;

$R_8$ is $C_1$-$C_6$ alkyl;

Y and Z are independently H, $NO_2$, $C_1$-$C_3$ alkoxy, $C_1$-$C_3$ alkylthio, Cl, Br, F, $C_1$-$C_4$ alkyl, $NH_2$ or $N(CH_3)_2$;

X is $$-\underset{CH_3}{\overset{}{C}HCH_2}-,\ -(CH_2)_n-,\ -CH_2\underset{CH_3}{\overset{}{C}H}-,\ -\underset{CH_3}{\overset{CH_3}{C}}=CH-,$$

$$-CH=CH-,\ -CH=\underset{CH_3}{\overset{CH_3}{C}}-,\ \text{or}\ -\underset{CH_3}{\overset{}{C}H}-;$$

n is 1, 2 or 3;

provided that:

(a) when Y and Z are H, then X is other than $$-CH_2-,\ -\underset{CH_3}{\overset{CH_3}{C}H}-\ \text{or}\ -CH_2CH_2CH_2-;$$

(b) when Y is other than $OCH_3$, then $R_6$ and $R_7$ are $CH_3$; and (c) when Y and Z are H and X is $$-CH=CH-,\ -\underset{}{\overset{CH_3}{C}H}=C-\ \text{or}\ -CH=\overset{CH_3}{C}-,$$

then $R_4$ is other than $NR_6R_7$.

2. A compound of according to claim 1, having the formula

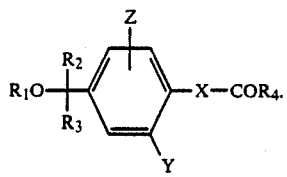

I

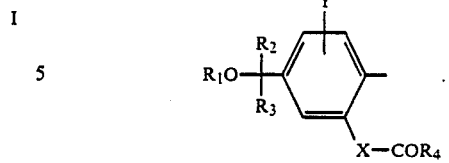

II

3. A compound of claim 2 wherein n is 1.

4. A compound of claim 2 where $R_1$ is H.

5. A compound of claim 2 where Y is $OCH_3$ or $OC_2H_5$.

6. A compound of claim 2 where Z is H.

7. A compound of claim 2 where X is $-CH_2CH_2-$.

8. A compound of claim 2 where $R_4 = OR_5$ or Cl.

9. A compound of claim 8 where $R_5$ is H, $CH_3$ or $C_2H_5$.

10. A compound of claim 2 where $R_4 = N(CH_3)_2$.

11. A compound of claim 2 where $R_2$ and $R_3$ are both $CF_3$.

12. A compound of claim 2 where $R_1$ is H;

Y is $OCH_3$ or $OC_2H_5$;

Z is H;

X is $-CH_2CH_2-$;

$R_4$ is OH, $OCH_3$, $OC_2H_5$, or $N(CH_3)_2$; and $R_2$ and $R_3$ are both $CF_3$.

13. The compound of claim 2 which is 3-{2-methoxy-4-[2,2,2-trifluoro-1-hydroxy-1-(trifluoromethyl)ethyl]-phenyl}propanoic acid.

14. The compound of claim 2 which is methyl 2-methoxy-4-[2,2,2-trifluoro-1-hydroxy-1-(trifluoromethyl)ethyl]benzenepropanoate.

15. The compound of claim 2 which is ethyl 2-methoxy-4-[2,2,2-trifluoro-1-hydroxy-1-(trifluoromethyl)ethyl]benzenepropanoate.

16. A compound according to claim 1, having the formula

17. A pharmaceutical composition consisting essentially of a suitable pharmaceutical carrier and an effective antihypertensive amount of a compound of claim 2 where $R_4$ is other than Cl.

18. A pharmaceutical composition consisting essentially of a suitable pharmaceutical carrier and an effective antihypertensive amount of a compound of claim 12 where $R_4$ is other than Cl.

19. A pharmaceutical composition consisting essentially of a suitable pharmaceutical carrier and an effective antihypertensive amount of a compound of claim 12 where $R_4$ is other than Cl.

20. A pharmaceutical composition consisting essentially of a suitable pharmaceutical carrier and an effective antihypertensive amount of a compound of claim 14 where $R_4$ is other than Cl.

21. A pharmaceutical composition consisting essentially of a suitable pharmaceutical carrier and an effective antihypertensive amount of a compound of claim 15 where $R_4$ is other than Cl.

22. A method of treating hypertension in mammals which comprises administering to the mammal an effective hypertensive amount of a compound of claim 2 where $R_4$ is other than Cl.

23. A method of treating hypertension in mammals which comprises administering to the mammal an effective hypertensive amount of a compound of claim 12 where $R_4$ is other than Cl.

24. A method of treating hypertension in mammals which comprises administering to the mammal an effective hypertensive amount of a compound of claim 13 where $R_4$ is other than Cl.

25. A method of treating hypertension in mammals which comprises administering to the mammal an effective hypertensive amount of a compound of claim 14 where $R_4$ is other than Cl.

26. A method of treating hypertension in mammals which comprises administering to the mammal an effective hypertensive amount of a compound of claim 15 where $R_4$ is other than Cl.

* * * * *